United States Patent [19]

Onishi

[11] Patent Number: 4,850,340
[45] Date of Patent: Jul. 25, 1989

[54] THERAPEUTIC MASSAGE DEVICE

[75] Inventor: Teruo Onishi, Hyogo, Japan

[73] Assignees: Nihondenjihachiryokikenkyusho Co., Ltd., Toyooka; Nihonkenkozoshinkenkyukai Co., Ltd., Fukuoka, both of Japan

[21] Appl. No.: 53,524

[22] Filed: May 19, 1987

Related U.S. Application Data

[63] Continuation of Ser. No. 741,664, Jul. 31, 1985, abandoned.

[51] Int. Cl.⁴ .......................... A61H 1/00; A61N 1/42
[52] U.S. Cl. .................................... 128/24.1; 128/48; 600/13; 600/15
[58] Field of Search ....................... 128/41, 48, 49, 32, 128/24 R, 24.1, 24.2, 384, 1.3, 1.5; 600/13–15, 9

[56] References Cited

U.S. PATENT DOCUMENTS

| 1,234,700 | 7/1917 | McLain | 128/41 |
| 2,135,312 | 11/1938 | Muckle | 128/24.2 |
| 3,323,517 | 6/1967 | Keller | 128/24.1 |
| 3,710,784 | 1/1973 | Taylor | 128/24.2 |
| 4,095,587 | 6/1978 | Ishikawa | 128/1.3 |
| 4,224,931 | 9/1980 | Nelkin | 128/32 |
| 4,396,011 | 8/1983 | Mack et al. | 128/36 |

FOREIGN PATENT DOCUMENTS 646314  11/1928  France .................................. 128/1.5

OTHER PUBLICATIONS

Mansfield et al, NMR Imaging in Biomedicine, Supplement 2, Academic Press, N.Y., Apr. 1982, pp. 297–310.

Primary Examiner—Francis Jaworski
Assistant Examiner—John C. Hanley
Attorney, Agent, or Firm—Jordan and Hamburg

[57] ABSTRACT

A device for applying heat and vibration to the body to relieve pain and stiffness and to enhance blood circulation. Individual hollow cases are pivotally coupled together in a stand of cases, the ends of which are coupled to belt portions adapted to be attached together to support the strand around a body member. Inside each case is a coil arrangement which, when electrically energized, produces heat and vibration that can be coupled to the body through the cases.

8 Claims, 3 Drawing Sheets

THERAPEUTIC MASSAGE DEVICE

This application is a continuation of application Ser. No. 741,664, filed July 31, 1985, now abandoned.

TECHNICAL FIELD

The present invention relates to a therapeutic apparatus generating magnetic field which treats pains, stiffness of body and other ailments of patients through enhancing blood circulation by continuous application of an alternating magnetic field to the affected portion of the body.

BACKGROUND OF THE INVENTION

Conventionally, a therapeutic apparatus generating magnetic field is constituted by housing and disposing a magnetic generator inside a case having a box or cylindrical shape and is constructed that a patient or a third person presses the apparatus on the affected portion of the patient's body by hand to apply the alternating magnetic field.

However, this type of apparatus can perform therapy on only a limited part of the body because of the narrow range of magnetic field that is applicable, and particularly where there is a wide range of affected parts, moving the apparatus is required. In addition, no sufficient effect of magnetic therapy is obtainable because of low intensity of magnetic field, and also due to a required hand operation, the maneuverability is poor, requiring much trouble in therapy, and thereby the operator gets fatigued. Thus the conventional apparatuses have disadvantages as mentioned above.

The present invention is intended to provide a novel therapeutic apparatus generating magnetic field which excels in the therapeutic effect and improves the maneuverability by adopting a construction wherein a plural number of magnetic generators are coupled and a range of magnetic field generators can be fixed to the patient's body.

SUMMARY OF THE INVENTION

The therapeutic apparatus of magnetic generator in accordance with the present invention is of a construction wherein magnetic field generators are housed and disposed in a plural number of cases respectively and respective cases are coupled by pivoting to one another in a freely rotatable fashion. In addition, the therapeutic apparatus generating magnetic field in accordance with the present invention is provided with a connecting member at both ends of each case, thereby being constituted so that it can be wound round and fixed to each part of the patient's body such as neck, waist, arm, leg, or the like.

In accordance with the present invention, fluctuating magnetic fields are generated individually from each magnetic field generator, and these magnetic field can be made to influence intensively the affected part in a wide range and in a manner to surround it. Accordingly, an excellent effect of magnetic therapy can be provided in comparison with the conventional instances, and also no special operation like moving the apparatus is required, meaning that the maneuverability is enhanced, thus effectively achieving the objective of the invention.

DETAILED DESCRIPTION OF THE PREFERRED EMBODIMENTS

Figure 1:
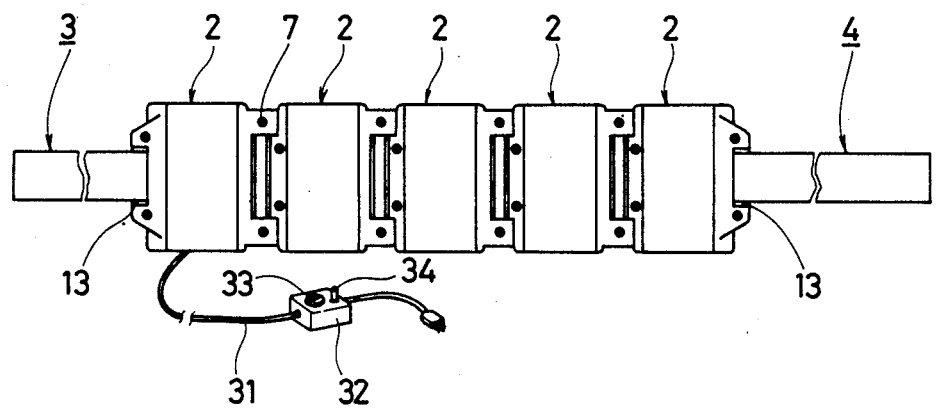
FIG. 1 is a front view showing an entire configuration of a therapeutic apparatus generating magnetic field in accordance with the present invention.
Figure 2:
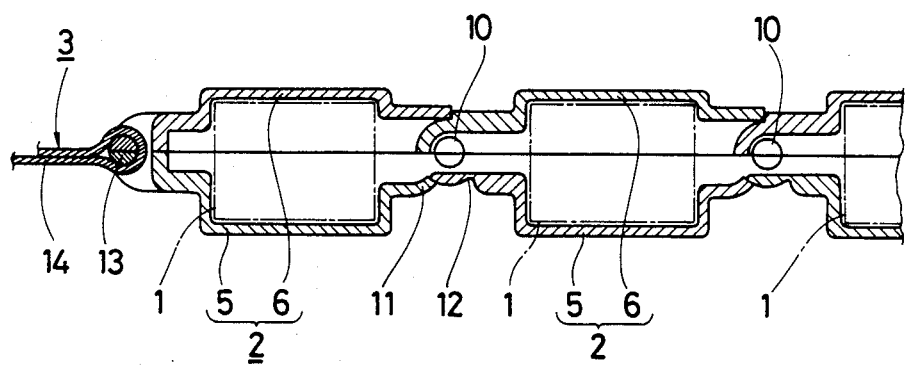
FIG. 2 is an enlarged horizontal cross-sectional view showing cases in a coupled state.
Figure 3:
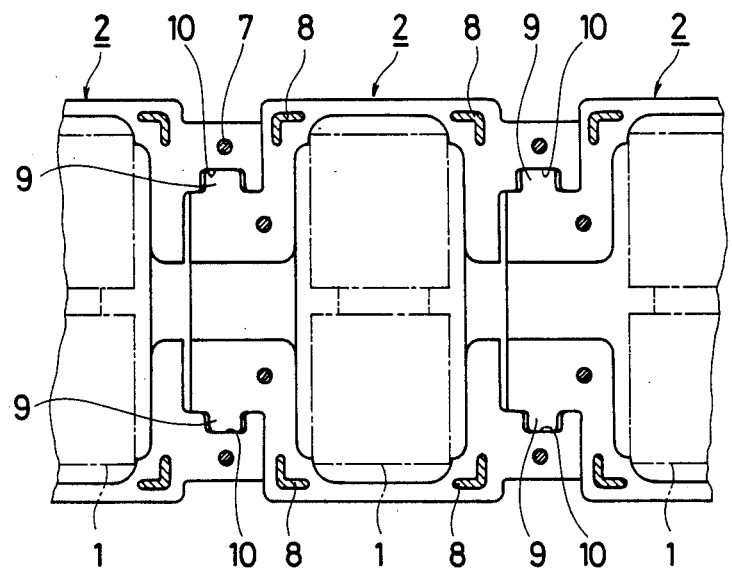
FIG. 3 is an enlarged vertical cross-sectional view showing cases in a coupled state.
Figure 4:
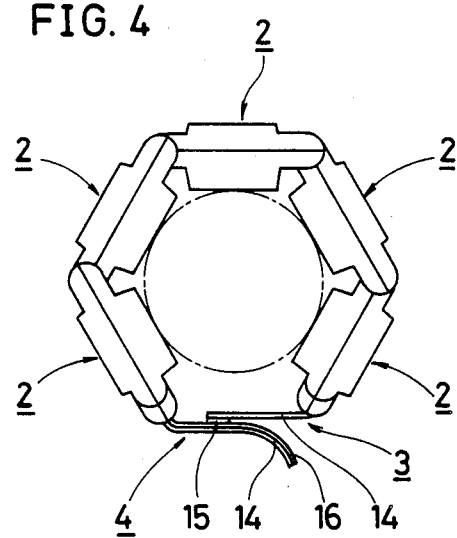
FIG. 4 is a plan view showing therapeutic apparatus generating magnetic field in use.

In the therapeutic apparatus generating magnetic field in accordance with the present invention as shown in FIG. 1 through FIG. 4, magnetic field generators 1 are housed and disposed inside a plural number of cases 2 respectively and each case is coupled in a line by pivoting, and also connecting members 3 and 4 capable of mutual connection are mounted on the cases 2 and 2 located at both ends.

Each case 2 is formed by placing open end faces of a pair of coupling elements 5 and 6 against each other and fixing a plural number of positions by screws 7. At the corners of open end faces of the respective coupling members 5 and 6, protruded lines 8 are provided on one face and grooves on the other face (not illustrated), and when the coupling members 5 and 6 are united one with another, the protruded lines 8 are engaged with the grooves.

On the side end face of each case 2, either of protruded axes 9 and 9 and the sustaining receiver holes 10 and 10 in the upward and downward directions are formed, and the protruded axes 9 are engaged with the sustaining receiver holes 10 between the adjacent cases 2 and 2, and thereby respective cases 2 and 2 are coupled with each other by pivoting in a freely rotatable fashion.

Furthermore, at the coupling part of respective cases 2 and 2, a contact piece 11 is formed on the protruded axis side respectively, and when the contact piece 11 is engaged with the stopping groove 12, rotation between cases 2 and 2 is limited.

On the cases 2 and 2 located at both ends, mounting axes 13 and 13 are provided at the outside end parts and belts 14 constituting the coupling members 3 and 4 are mounted on the respective mounting axes 13 and 13. At the tip of one belt 14 and along the whole length of the other belt 14 are mounted face fasteners 15 and 16 interlocking with each other, and the belts 14 and 14 are coupled by interlocking these face fasteners 15 and 16 with each other, and thereby the therapeutic apparatus can be wound around and fixed to the proper portion of the patient's body. Furthermore, the coupling members 3 and 4, in accordance with the present invention can undergo a proper change in design such as providing connecting metal fittings at the tip of each belt 14 or the like, not limited to the above-mentioned embodiment.

Figure 5:
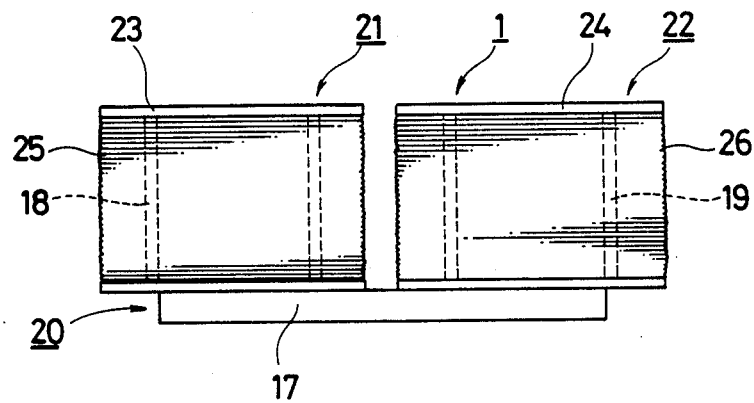
FIG. 5 is a front view showing a configuration of a magnetic field generator.
Figure 6:
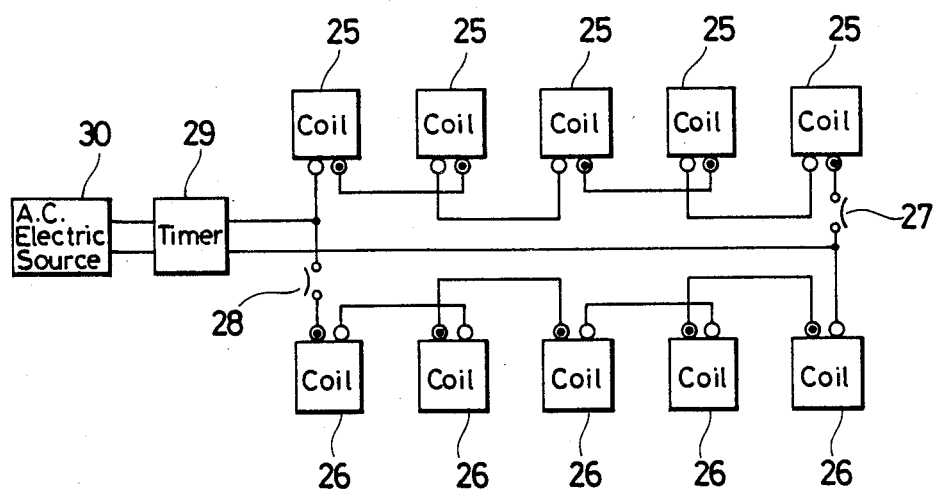
FIG. 6 is a block diagram showing an electric wiring of a therapeutic apparatus generating magnetic field.

The above-mentioned magnetic field generator 1, as is shown in FIG. 5, is composed of laminated iron core 20 provided with leg parts 18 and 19 at both ends of a base board 17 and coil bobbins 21 and 22 engaged with respective leg parts 18 and 19. The coil bobbins 21 and 22 are formed by winding coils 25 and 26 around frames with flanges 23 and 24 respectively, and are fixed to the hollow inner part of the case 2 with the tip faces of the leg parts 18 and 19 facing the above-mentioned one of coupled bodies. Coils 25 and 26 of both coil bobbins 21 and 22 are connected in a manner such that the alternating magnetic fields generated by energizing are intensified by each other, and as shown in FIG. 6, respective coils 25 and 26 in each magnetic field generator 1 are connected in series in turn. In the coil connected circuit, thermostats 27 and 28 limiting rises in temperature of the coils 25 and 26 are installed. This circuit is connected to an AC supply 30 through a timer 29 and an arbitrary operation time is set by the timer 29. This timer 29 is, as shown in FIG. 1, housed and disposed in a control case 32 mounted on the tip of a lead-out wire 31 and a knob 33 for time setting and a power switch 34 are disposed on the upper surface of the case 32.

UTILITY IN THERAPY

In the case of employing the therapeutic apparatus generating magnetic field, the apparatus is mounted and fixed to the affected portion of the patient's body where stiffness, pain or other ailment is felt in a manner such that the therapeutic apparatus is wound around it. Subsequently, the timer 29 is set with the knob 33, and thereby the respective coils 25 and 26 of each magnetic field generator 1 are energized and the superposed magnetic fluxes of both coils 25 and 26 act on the patient's body from the end faces of the leg parts 18 and 19 of the iron core 20. At the same time, each case 2 vibrates, and this vibration exerts a massaging effect on the body, and also a warming effect is given by the generation of heat. The magnetic field generator 1 acts intensively on the affected portion in a wide range and in a manner to surround it, thereby enhancing the circulation of the blood at the portion where stiffness or pain is felt to relieve the condition of stiffness or pain.

What is claimed is:

1. Apparatus comprising a plurality of hollow cases, each of said cases having a first half section and a second half section, each of said first and second half sections having mating surfaces which mate with one another, securing means passing through said mating surfaces to secure said first and second half sections together, each of said plurality of cases having a main portion and two opposed end portions, one of said end portions having a pair of spaced legs extending from said main portion, the other of said end portions having a central extension, said central extension of one case extending into the space between two legs of another like case, said legs having opposed and axially aligned receiving openings facing each other, said central extension having lateral aligned protrusions such that the lateral algined protrusions of one case is received in the axially aligned openings of another like case to thereby provide a pivotal support between two like cases, each of said cases having a contact part and a stopping part arranged such that the contact part of one case is engageable with the stopping part of another like case to limit the extent of relative pivotal movement between two like cases, said plurality of cases being pivotably connected together as aforesaid to define an elongated strand of like pivotably connected cases having two end cases, an end case means pivotally connected to each of said end cases of said strand of like cases, and a belt connected to each of said two end case means such that said strand of like cases, said two end case means, and said belt are pivotably connected in series so as to be capable of being formed into a closed loop which can be encircled and secured in place about a part of a person's body, each of said like cases and each of said end case means having a hollow interior, electric coil means disposed in and fixed to each of said hollow interiors, each of said electric coil means comprising a base and first and second spaced leg parts extending from said base, and first and second coils wound about said first and second leg parts respectively, electric connecting means connecting said electric coil means to an A.C. source such that all of said first coils are connected in series and all of said second coils are connected in series, said electric connecting means further comprising a thermostat for controlling the temperature of said electric coil means, said electric connecting means further comprising a timer for setting a time for connecting and disconnecting said electric coil means to and from said A.C. source.

2. Apparatus comprising a plurality of hollow cases, each of said cases having a first half section and a second half section, each of said first and second half sections having mating surfaces which mate with one another, the mating surface of one of said first and second half sections having protrusions and the mating surface of the other of said first and second half sections having depressions which receive said protrusions, securing means passing through said mating surfaces to secure said first and second half sections together, each of said plurality of cases having a main portion and two opposed end portions, one of said end portions having a pair of spaced legs extending from said main portion, the other of said end portions having a central extension, said central extension of one case extending into the space between two legs of another like case, said legs having opposed and axially aligned receiving openings facing each other, said central extension having lateral aligned protrusions such that the lateral aligned protrusions of one case is received in the axially aligned openings of another like case to thereby provide a pivotal support between two like cases, each of said cases having a contact part and a stopping part arranged such that the contact part of one case is engageable with the stopping part of another like case to limit the extent of relative pivotal movement between two like cases, said plurality of cases being pivotably connected together as aforesaid to define an elongated strand of like pivotably connected cases having two end cases, two end case means, one of said end case means being pivotally connected to each of said two end cases of said strand of like pivotally connected cases, and a belt pivotably connected to each of said two end case means such that said strand of like cases, said two end case means and said belt are pivotably connected in series so as to be capable of being formed into a closed loop which can be encircled and secured in place about a part of a person's body, each of said like cases and each of said end case means having a hollow interior, electric coil means disposed in and fixed to said hollow interiors, said electric coil means comprising a base and first and second spaced leg parts extending from said base, first and second coils wound about said first and second leg parts respectively, each of said first and second spaced leg parts having ends, and flagnes mounted on each of said ends, said electric coil means being disposed in said hollow interior of said cases such that said ends of said spaced leg parts face one of said first or second half sections, electric connecting means connecting said electric coil means to an A.C. source such that all of said first coils are connected in series and all of said second coils are connected in series, said electric connecting means further comprising a thermostat for controlling the temperature of said electric coil means, said electric connecting means further comprising a timer for setting a time for connecting and disconnecting said electric coil means to and from said A.C. source.

3. Apparatus according to claim 2 wherein each of said end case means has a third half section and a fourth half section, each of said third and fourth half sections having second mating surfaces which mate with one another, said second mating surface of one of said third and fourth half sections having second protrusions and said second mating surface of the other of said third and fourth half sections having second depressions which receive said second protrusions, fastening means passing through said second mating surfaces to secure said third and fourth half sections together, each of said two end case means having a second main portion and two opposed second end portions, one of said two second end portions of one of said two end case means having a second pair of spaced legs extending from its second main portion and pivotably mounting said central extension of one of said two end cases, the other of said two second end portions of said one case means being connected to said belt, one of said second end portions of the other of said two end case means having a second central extension extending from its second main portion and pivotably mounting said spaced legs of the other of said two end cases, the other of said two second end portions of said other case end means being connected to said belt.

4. Apparatus comprising a plurality of hollow cases, each of said cases having a first half section and a second half section, each of said first and second half sections having mating surfaces which mate with one another, securing means passing through said mating surfaces to secure said first and second half sections together, each of said plurality of cases having a main portion and two opposed end portions, one of said end portions having a pair of spaced legs extending from said main portion, the other of said end portions having a central extension, said central extension of one case extending into the space between two legs of another like case, said legs having opposed and axially aligned receiving openings facing each other, said central extension having lateral aligned protrusions such that the lateral aligned protrusions of one case is received in the axially aligned openings of another like case to thereby provide a pivotal support between two like cases, each of said cases having a contact part and a stopping part arranged such that the contact part of one case is engageable with the stopping part of another like case to limit the extent of relative pivotal movement between two like cases, said plurality of cases being pivotably connected together as aforesaid to define an elongated strand of like pivotably connected cases having two end cases, an end case means pivotally connected to each of said end cases of said strand of like pivotally connected cases, and a belt connected to each of said two end case means such that said strand of like cases, said two end case means, and said belt are pivotably connected in series so as to be capable of being formed into a closed loop which can be encircled and secured in place about a part of a person's body, each of said like cases and each of said end case means having a hollow interior, electric operated heating and vibration means disposed in and fixed to each of said hollow interiors, electric connecting means connecting said electric operated heating and vibration means to an A.C. source, said electric connecting means further comprising a thermostat for controlling the temperature of said electric operated heating and vibration means, said electric connecting means further comprising a thermostat for controlling the temperature of said electric operated heating and vibration means, said electric connecting means further comprising a timer for setting a time for connecting and disconnecting said electric operated heating and vibration means to and from said A.C. source.

5. Apparatus comprising a plurality of hollow cases, each of said cases having a first half section and a second half section, each of said first and second half sections having mating surfaces which mate with one another, securing means passing through said mating surfaces to secure said first and second half sections together, each of said plurality of cases having a main portion and two opposed end portions, one of said end portions having a pair of spaced legs extending from said main portion, the other of said end portions having a central extension, said central extension of one case extending into the space between two legs of another like case, said legs having opposed and axially aligned receiving openings facing each other, said central extension having lateral aligned protrusions such that the lateral aligned protrusions of one case is received in the axially aligned openings of another like case to thereby provide a pivotal support between two like cases, each of said cases having a contact part and a stopping part arranged such that the contact part of one case is engageable with the stopping part of another like case to limit the extent of relative pivotal movement between two like cases, said plurality of cases being pivotably connected together as aforesaid to define an elongated strand of like pivotally connected cases, and a belt connected to each of said two end case means such that said strand of like cases, said two end case means, and said belt are pivotably connected in series so as to be capable of being formed into a closed loop which can be encircled and secured in place about a part of a person's body, each of said like cases and each of said end case means having a hollow interior, electric heating means disposed in and fixed to each of said hollow interiors, electric connecting means connecting said electric heating means to an A.C. source, said electric connecting means further comprising a thermostat for controlling the temperature of said electric heating means, said electric connecting means further comprising a timer for setting a time for connecting and disconnecting said electric heating means to and from said A.C. source.

6. A therapeutic apparatus comprising a plurality of hollow cases, each of said cases having a first half section and a second half section, each of said first and second half sections having mating surfaces which mate with one another, securing means passing through said mating surfaces to secure said first and second half sections together, each of said plurality of cases having a main portion and two opposed end portions, one of said end portions having a pair of spaced legs extending from said main portion, the other of said end portions having a central extension, said central extension of one case extending into the space between two legs of another like case, said legs having opposed and axially aligned receiving openings facing each other, said central extension having lateral aligned protrusions such that the lateral aligned protrusions of one case is received in the axially aligned openings of another like case to thereby provide a pivotal support between two like cases, each of said cases having a contact part and a stopping part arranged such that the contact part of one case is engageable with the stopping part of another like case to limit the extent of relative pivotal movement between two like cases, said plurality of cases being pivotably connected together as aforesaid to define an elongated strand of like pivotably connected cases having two end cases, an end case means pivotably connected to each of said end cases of said strand of like cases, and a belt connected to each of said two end case means such that said strand of like cases, said two end case means, and said belt are pivotably connected in series so as to be capable of being formed into a closed loop which can be encircled and secured in place about a part of a person's body, each of said like cases and each of said end case means having a hollow interior, a magnetic field generator comprising electric coil means disposed in and fixed to each of said hollow interiors, each of said electric coil means comprising a base and first and second spaced leg parts extending from said base, and first and second coils wound about said first and second leg parts respectively, electric connecting means connecting said electric coil means to an A.C. source such that all of said first coils are connected in series and all of said second coils are connected in series, said electric connecting means further comprising a thermostat for controlling the temperature of said electric coil means, said electric connecting means further comprising a timer for setting a time for connecting and disconnecting said electric coil means to and from said A.C. source.

7. A therapeutic apparatus comprising a plurality of hollow cases, each of said cases having a first half section and a second half section, each of said first and second half sections having mating surfaces which mate with one another, the mating surface of one of said first and second half sections having protrusions and the mating surface of the other of said first and second half sections having depressions which recieve said protrusions, securing means passing through said mating surfaces to secure said first and second half sections together, each of said plurality of cases having a main portion and two opposed end portions, one of said end portions having a pair of spaced legs extending from said main portion, the other of said end portions having a central extension, said central extension of one case extending into the space between two legs of another like case, said legs having opposed and axially aligned receiving openings facing each other, said central extension having lateral aligned protrusions such that the lateral aligned protrusions of one case is received in the axially aligned openings of another like case to thereby provide a pivotal support between two like cases, each of said cases having a contact part and a stopping part arranged such that the contact part of one case is engageable with the stopping part of another like case to limit the extent of relative pivotal movement between two like cases, said plurality of cases being pivotably connected together as aforesaid to define an elongated strand of like pivotably connected cases having two end cases, two end case means, one of said end case means being pivotably connected to each of said two end cases of said strand of like pivotably connected cases, and a belt pivotably connected to each of said two end case means such that said strand of like cases, said two end case means and said belt are pivotably connected in series so as to be capable of being formed into a closed loop which can be encircled and secured in place about a part of a person's body, each of said like cases and each of said end case means having a hollow interior, a magnetic field generator comprising electric coil means disposed in and fixed to said hollow interiors, said electric coil means comprising a base and first and second spaced leg parts extending from said base, first and second coils wound about said first and second leg parts respectively, each of said first and second spaced leg parts having ends and flanges mounted on each of said ends, said electric coil means being disposed in said hollow interior of said cases such that said ends of said spaced leg parts face one of said first or second half sections, electric connecting means connecting said electric coil means to an A.C. source such that all of said first coils are connected in series and all of said second coils are connected in series, said electric connections means further comprising a thermostat for controlling the temperature of said electric coil means, said electric connecting means further comprising a timer for setting a time for connecting and disconnecting said electric coil means to and from said A.C. source.

8. A therapeutic apparatus according to claim 7, wherein each of said end case means has a third half section and a fourth half section, each of said third and fourth half sections having second mating surfaces which mate with one another, said second mating surface of one of said third and fourth half sections having second protrusions and said second mating surface of the other of said third and fourth half sections having second depressions which receive said second protrusions, fastening means passing through said second mating surfaces to secure said third and fourth half sections together, each of said two end case means having a second main portion and two opposed second end portions, one of said two second end portions of one of said two end case menas having a second pair of spaced legs extending from its second main portion and pivotably mounting said central extension of one of said two end cases, the other of said two second end portions of said one case means being connected to said belt, one of said second end portions of the other of said two end case means having a second central extension extending from its second main portion and pivotably mounting said spaced legs of the other of said two end cases, the other of said two second end portions of said other case end means being connected to said belt.

* * * * *